United States Patent [19]

Schwartz, deceased

[11] Plant 4,693

[45] Apr. 21, 1981

[54] ROSE PLANT

[75] Inventor: Ernest Schwartz, deceased, late of Kingsville, Md., by Hazel E. Schwartz, executrix

[73] Assignee: F. Harmon Saville, Nor'East Miniature Roses, Rowley, Mass.

[21] Appl. No.: 93,627

[22] Filed: Nov. 13, 1979

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new burnt orange and yellow bicolor miniature rose which lightens to pinkish white tonality upon aging.

1 Drawing Figure

1

The present invention relates to a new and distinct variety of rose plant of the miniature rose class, which was originated by my crossing as seed parent a seedling which is the product of the following cross: [(Grand Opera × Zorina) × unnamed miniature seedling] and a seedling of the cross Harry Wheatcroft × Magic Carrousel as pollen parent.

Among the novel characteristics possessed by this new variety which distinguish it from its parents and all other varieties of which I am aware are: (1) unusual burnt orange and yellow bicoloring borne primarily singly to a stem in a manner typical of hybrid tea plants and also blooming on long stems, (2) small, petite-size blooms for this color range as compared to preexisting varieties and (3) a compact, well branched, well rounded plant. Asexual reproduction by budding of the new variety as performed in Essex County, Massachusetts, shows that the foregoing and other distinguishing characteristics come true to form and are established and transmitted through succeeding propagations.

The new and improved rose variety which I have developed is an unusual miniature rose in its coloring and small size of blooms combining attractive flowers and verdant foliage. Like hybrid teas, the flowers are singly-borne and delightfully displayed on long stems. The changing colors upon aging result in an eye-catching plant for display with varying color tones often visible at the same time. From burnt orange and distinct yellow tones the flowers age to a pale pinking white.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g, "31A" is plate 31A of the Royal Horticultural Society Color Chart.

Parentage: Seedling.

*Seed parent.*—(Grand Opera × Zorina) × unnamed seedling.

*Pollen parent.*—Harry Wheatcroft × Magic Carrousel.

Class: Miniature.

2

The following observations are made of specimens grown in Essex County, Mass., during the month of August.

I. FLOWER

Blooming habit: Fast recurrent, near continuous.

A. *Bud.*—(1) Size: Small. (2) Form: Ovate. (3) Color: When sepals first divide — 31A or 31B on top side of petals, underside is a little lighter burnt orange shading to a near 11A to 12A color at and near point of petal attachment. (4) Sepals: Foliated, sometimes much longer than bud. (5) Peduncle: Length — about ⅝ to ¾ inches, good proportion to bloom. Aspect — straight. Strength — erect, strong. Color — 144B.

B. *Bloom.*—(1) Size: Average size when fully expanded — about ⅝ to ¾ inches. (2) Borne: Primarily singly. (3) Form: Cupped, becoming flat upon opening. (4) Petalage: Number of petals under normal conditions—about 20 to 30. (5) Color: (during first two days). The predominant color seen as sepals unfurl is burnt orange 31A to 31B. The reverse surface (petal underside) shows yellow at the petal base near the point of attachment. As the bloom opens, the bicoloring becomes very visible and the yellow coloring of the upper petal surface predominates with the burnt orange coloring appearing most evident at the petal edge and shading to yellow at petal interior. The yellow coloring seems near to 11A or 12A. The center of the just fully-opened flower appears deep yellow in part because of the visible stamen and pollen coloring (16A and 17B). (6) Color Change: As bloom ages — the fully open bloom lightens considerably with the burnt orange petal-edge coloring becoming pinkish and the yellow coloring lightening toward white. The overall effect is a pinkish white tonality (36D or C) with occasional darkening of petal edges.

C. *Petals.*—(1) Texture: Relatively thick. (2) Appearance: Inside — satiny: Outside — satiny. (3) Form: Usually rounded (not pointed) at outer edge, roughtly tear drop shaped. (4) Arrangement: Shingle-like. (5) Petaloids in center: From none to 10 or more. (6) Persistence: Drop cleanly. (7) Fragrance: Light. (8) Lasting quality: Long on plant and as cut flower.

2. REPRODUCTIVE ORGANS

A. Stamens, filaments and anthers:
(1) *Arrangement.*—Stamens regularly arranged around styles.
(2) *Color.*—16A.
B. Pollen: Color — 17B.
C. Styles: Even, medium length.
D. Stigmas: Color — 163B.
E. Hips: None observed.

3. PLANT

A. Form: Compact, well rounded.
B. Growth: Vigorous, uniform branching. Height attained — 5 to 6 inches.
C. Foliage: Compound 5 to 7 leaflet leaves.
(1) *Size.*—Small.
(2) *Quantity.*—Abundant.
(3) *Color.*—Upper side — variable, 133A or B, sometimes 135A or B and 137A or B. Under side — 147C.
(4) *Shape.*—Pointed, oval.
(5) *Texture.*—Upper side — satiny. Under side — matte.
(6) *Edge.*—Serrated.
(7) *Serration.*—Regular, moderate.

(8) *Leaf stem.*—Color — near to 143A. Under side — near to 146C.
(9) *Stipules.*—Relatively long, and attached for ¾ of their length.
(10) *Resistance to disease.*—Blackspot — good. Mildew — good.
D. Wood:
(1) *New wood.*—Color — near 143C. Bark — smooth.
(2) *Old wood.*—Color — near to 143B. Bark — smooth.
E. Thorns:
(1) *Thorns.*—Quantity — relatively few. On laterals from stalk — practically none. Form — long, thin, pointed, slightly downward curve. Length — short. Color (when young) — 145C. Position — irregular.
(2) *Prickles.*—None.
F. Winter hardiness: Needs some protection in extreme climate.

I claim:

1. A new and distinct variety of rose plant of the miniature class, substantially as shown and described, characterized particularly by burnt orange and yellow bicolor blooms borne primarily singly to a stem on a compact, well rounded plant of attractive foliage.

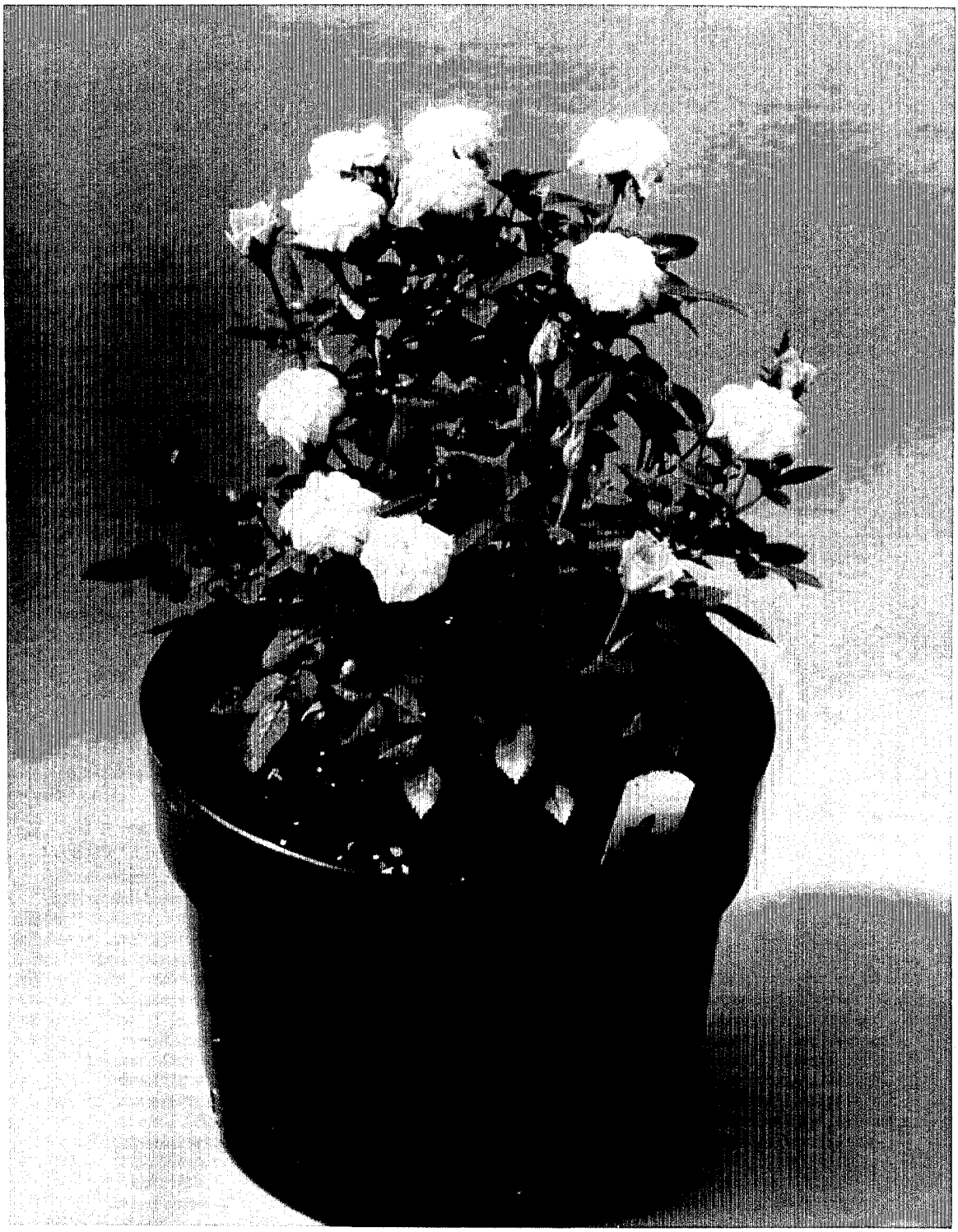

* * * * *